(12) United States Patent
Hoegh et al.

(10) Patent No.: US 8,364,286 B2
(45) Date of Patent: *Jan. 29, 2013

(54) LEAD ELECTRODE FOR USE IN AN MRI-SAFE IMPLANTABLE MEDICAL DEVICE

(75) Inventors: Thomas Barry Hoegh, Edina, MN (US); Stephen Lo Bolea, Watertown, MN (US); Carl D. Wahlstrand, Lino Lakes, MN (US); Gregory A. Hrdlicka, Plymouth, MN (US); James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/004,009

(22) Filed: Jan. 10, 2011

(65) Prior Publication Data

US 2011/0112615 A1    May 12, 2011

Related U.S. Application Data

(63) Continuation of application No. 11/009,862, filed on Dec. 10, 2004, now Pat. No. 7,877,150.

(60) Provisional application No. 60/557,991, filed on Mar. 30, 2004.

(51) Int. Cl.
*A61N 1/36* (2006.01)
(52) U.S. Cl. .................................................. 607/119
(58) Field of Classification Search .................. 607/119, 607/122
See application file for complete search history.

(56) References Cited

U.S. PATENT DOCUMENTS 7,877,150 B2 * 1/2011 Hoegh et al. ................. 607/119

* cited by examiner

*Primary Examiner* — Scott Getzow
*Assistant Examiner* — Amanda Patton

(57) ABSTRACT

A neurostimulation lead is configured to be implanted into a patient's body and has at least one distal electrode. The lead comprises at least one conductive filer electrically coupled to the distal electrode, a jacket for housing the conductive filer and a shield surrounding at least a portion of the filer for reducing electromagnetic coupling to the filer.

14 Claims, 9 Drawing Sheets

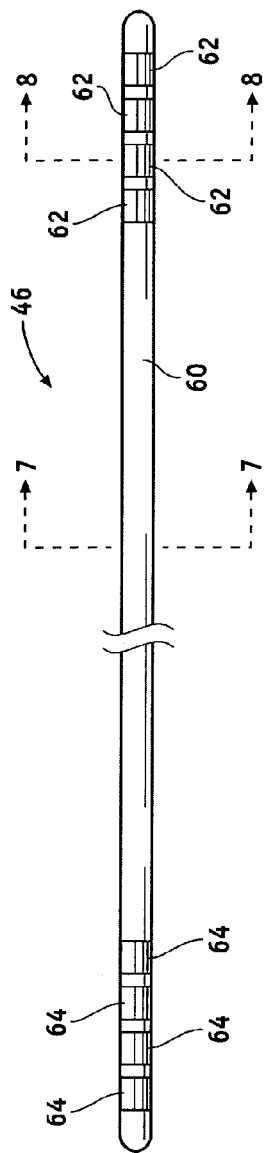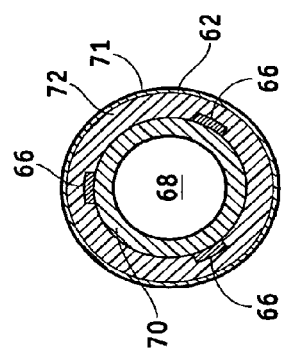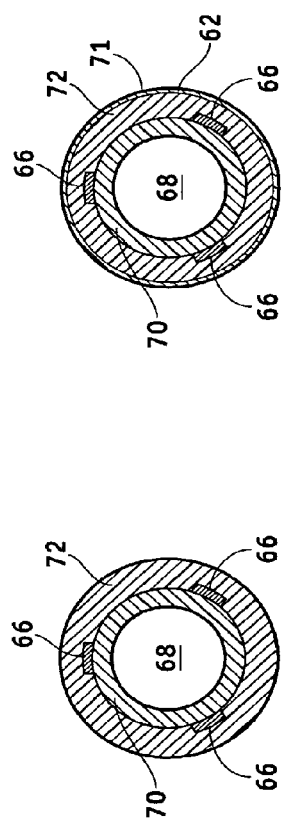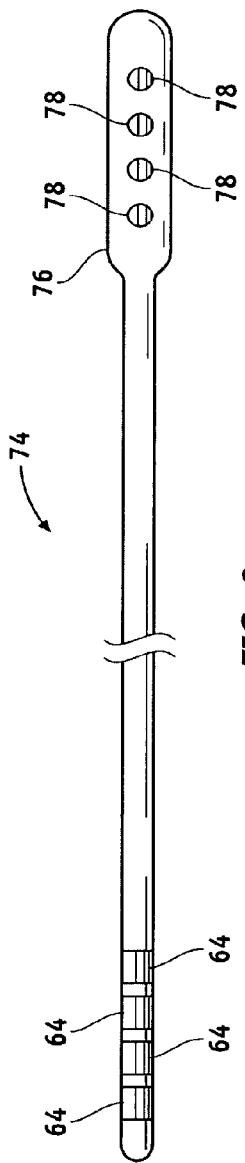

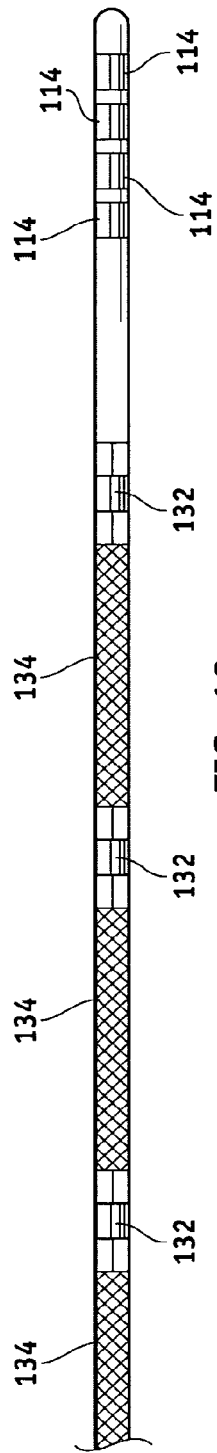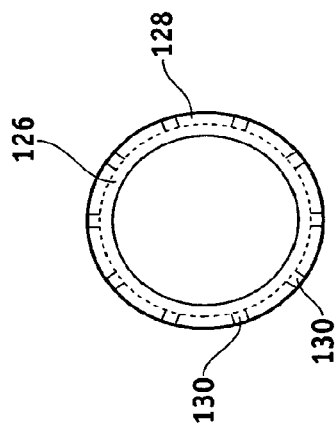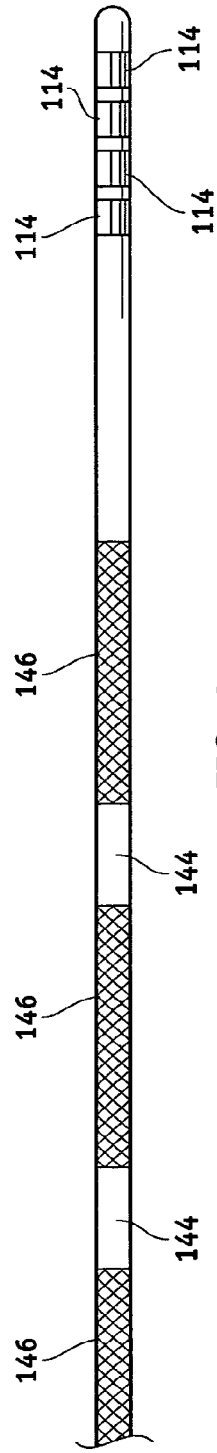

LEAD ELECTRODE FOR USE IN AN MRI-SAFE IMPLANTABLE MEDICAL DEVICE

CROSS REFERENCES TO RELATED APPLICATONS

The present application is a continuation of U.S. patent application Ser. No. 11/009,862, now U.S. Pat. No. 7,877, 150, filed on Dec. 10, 2004, and entitled Lead Electrode for Use in an MRI-Safe Implantable Medical Device, which is incorporated by reference herein and which claims the benefit of U.S. Provisional Application No. 60/557,991 filed Mar. 30, 2004, which is also incorporated by reference herein.

FIELD OF THE INVENTION

The present invention generally relates to implantable medical devices, and more particularly to an implantable MRI-safe shielded lead for use in conjunction with an implantable medical device that reduces the energy induced in the lead at MRI frequencies resulting in a corresponding decrease in the generation of unwanted heat at the lead's stimulation electrodes.

BACKGROUND OF THE INVENTION

Implantable medical devices are commonly used today to treat patients suffering from various ailments. Such implantable devices may be utilized to treat conditions such as pain, incontinence, sleep disorders, and movement disorders such as Parkinson's disease and epilepsy. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer. Current systems generally include a non-rechargeable primary cell neurostimulator, a lead extension, and a stimulation lead, and the two main classes of systems may be referred to as: (1) Spinal Cord Stimulation (SCS) and (2) Deep Brain Stimulation (DBS).

An SCS stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinbelow) currently contains from one to eight electrodes. Each extension (likewise to be discussed in detail below) is plugged into or connected to the neurostimulator at a proximal end thereof and is coupled to and interfaces with the lead or leads at a distal end of the extension.

The implanted neurostimulation system is configured to send mild electrical pulses to the spinal cord. These electrical pulses are delivered through the lead or leads to regions near the spinal cord or a nerve selected for stimulation. Each lead includes a small insulated wire coupled to an electrode at the distal end thereof through which the electrical stimulation is delivered. Typically, the lead also comprises a corresponding number of internal wires to provide separate electrical connection to each electrode such that each electrode may be selectively used to provide stimulation. Connection of the lead to an extension may be accomplished by means of a connector block including, for example, a series or combination of set screws, ball seals, etc. The leads are inserted into metal set screw bocks, and the metal set screws are manipulated to press the contacts against the blocks to clamp them in place and provide electrical connection between the lead wires and the blocks. Such an arrangement is shown in U.S. Pat. No. 5,458,629 issued Oct. 17, 1995 and entitled "Implantable Lead Ring Electrode and Method of Making".

A DBS system comprises similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to eight electrodes and, as was the case previously, the proximal end of the lead may be connected to the distal end of the extension and may be held in place by set screws. The proximal portion of the extension plugs into the connector block of the neurostimulator.

Magnetic resonance imaging (MRI) is a relatively new and efficient technique that may be used in the diagnosis of many neurological disorders. It is an anatomical imaging tool which utilizes non-ionizing radiation (i.e. no x-rays or gamma rays) and provides a non-invasive method for the examination of internal structure and function. For example, MRI permits the study of the overall function of the heart in three dimensions significantly better than any other imaging method. Furthermore, imaging with tagging permits the non-invasive study of regional ventricular function.

MRI scanning is widely used in the diagnosis of injuries to the head. In fact, the MRI is now considered by many to be the preferred standard of care, and failure to prescribe MRI scanning can be considered questionable. Approximately sixteen million MRIs were performed in 1996, followed by approximately twenty million in the year 2000. It is projected that forty million MRIs will be performed in 2004.

In an MRI scanner, a magnet creates a strong magnetic field which aligns the protons of hydrogen atoms in the body and then exposes them to radio frequency (RF) energy from a transmitter portion of the scanner. This spins the various protons, and they produce a faint signal that is detected by a receiver portion of the scanner. A computer renders these signals into an image. During this process, three electromagnetic fields are produced; i.e. (1) a static magnetic field, (2) a gradient magnetic field, and (3) a radio frequency (RF) magnetic field. The main or static magnetic field may typically vary between 0.2 and 3.0 Tesla. A nominal value of 1.5 Tesla is approximately equal to 15,000 Gauss which is 30,000 times greater than the Earth's magnetic field of approximately 0.5 Gauss. The time varying or gradient magnetic field may have a maximum strength of approximately 40 milli-Tesla/meters at a frequency of 0-5 KHz. The RF may, for example, produce thousands of watts at frequencies of between 8-215 MHz. For example, up to 20,000 watts may be produced at 64 MHz and a static magnetic field of 1.5 Tesla; that is, 20 times more power than a typical toaster. Thus, questions have arisen regarding the potential risk associated with undesirable interaction between the MRI environment and the above-described neurostimulation systems; e.g. forces and torque on the implantable device within the MRI scanner caused by the static magnetic field, RF-induced heating, induced currents due to gradient magnetic fields, device damage, and image distortion. Of these interactions, the problems associated with induced RF currents in the leads are most deserving of attention since it has been found that the temperature in the leads can rise by as much as 25° Centigrade or higher in an MRI environment.

A similar problem occurs when a patient undergoes diathermy treatment employing RF energy to create eddy currents in the patient's tissue so as to heat the tissue and promote healing. In this environment, current may also be produced in the implanted lead causing undesirable heating of the electrodes as described above.

Accordingly, it would be desirable to provide an implantable medical device that may be safely operated in an MRI environment. It would be further desirable to provide an implantable medical device such as a SCS or DBS neurostimulation system that may be operated in an MRI environment without the generation of significant heat in the leads due to induced RF currents. It would be further desirable to provide an MRI-safe, implantable lead that may be used in conjunction with known implantable medical devices that reduces the coupling between the lead and the electromagnetic fields produced in an MRI environment thereby reducing the generation of unwanted heat at the leads stimulation electrodes. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

According to an aspect of the invention, there is provided a neurostimulation lead configured to be implanted into a patient's body and having at least one distal electrode. The lead comprises at least one conductive filer electrically coupled to the distal electrode, a jacket for housing the conductive filer, and a shield surrounding at least a portion of the filer for reducing electromagnetic coupling to the filer.

According to a further aspect of the invention, there is provided a neurostimulation lead configured to be implanted into a patient's body and having at least one distal electrode. The lead comprises at least one conductive filer electrically coupled to the distal electrode and a multi-layer jacket surrounding the filer for shielding the filer from electromagnetic energy, the multi-layer jacket comprising alternating layers of conductive and non-conductive material.

According to a still further aspect of the invention, there is provided a pulse stimulation system configured for implantation into a patient's body. The system comprises a conductive encasement, a pulse generator within the encasement, at least one conductive filer having a proximal end electrically coupled to the pulse generator and having a distal end. At least one stimulation electrode is electrically coupled to the distal end. A jacket is provided for housing the conductive filer and a shield surrounds at least a portion of the filer for reducing electromagnetic coupling to the filer.

BRIEF DESCRIPTION OF THE DRAWINGS

The present invention will hereinafter be described in conjunction with the following drawing figures, wherein like numerals denote like elements, and:

FIG. 6 is a top view of the lead shown in FIG. 2;

FIGS. 7 and 8 are cross-sectional views taken along lines 7-7 and 8-8, respectively, in FIG. 6;

FIG. 9 is a top view of an alternate lead configuration;

FIG. 16 is a cross-sectional view of a composite jacket/shield in accordance with the present invention;

FIG. 17 is a cross-sectional view of a second embodiment of the present invention;

FIG. 18 is a side view of yet another embodiment of the present invention utilizing a segmented shield;

FIG. 21 is a side view of a segmented shield in accordance with the present invention wherein the length of each segment is substantially one-quarter wavelength.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
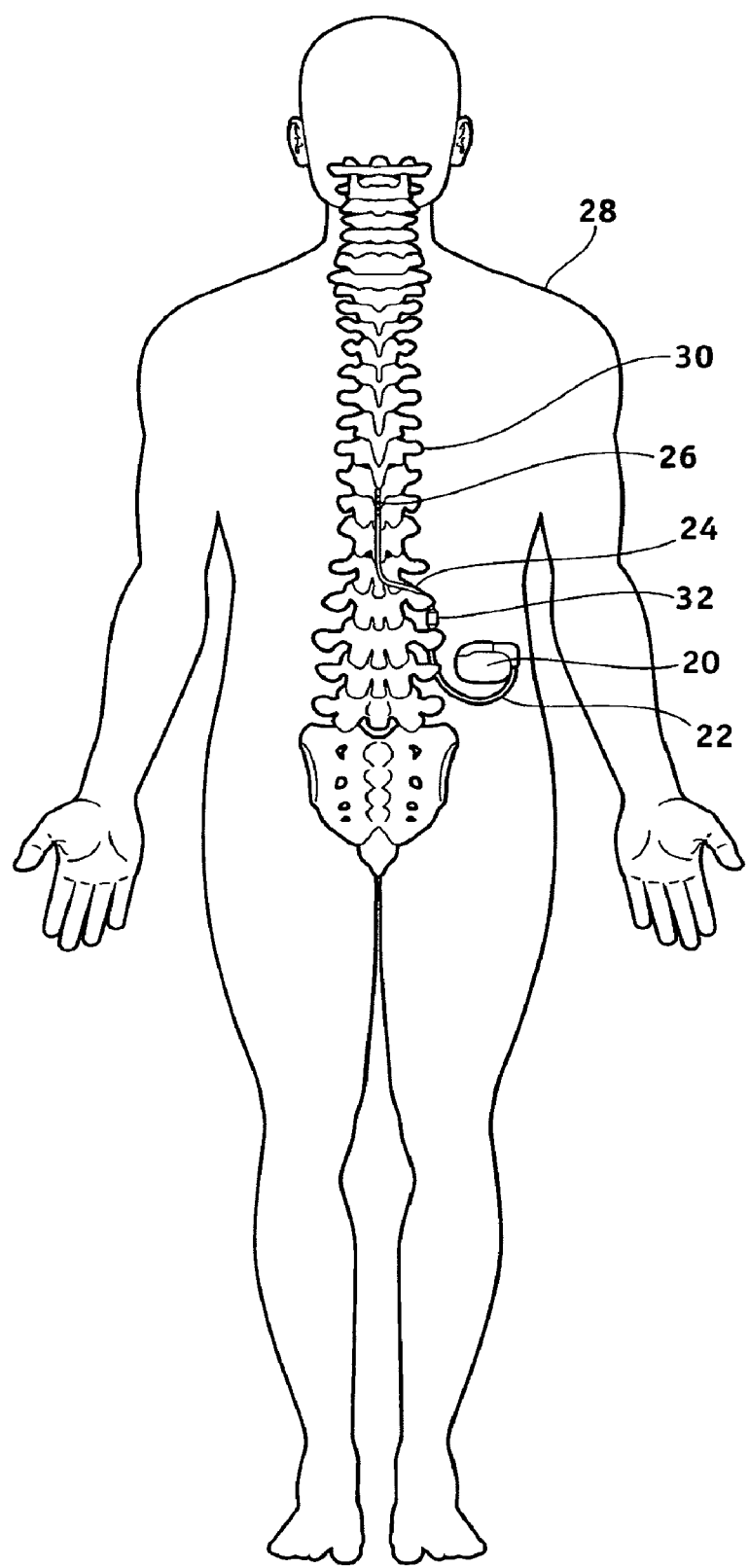
FIG. 1 illustrates a typical spinal cord stimulation system implanted in a patient.

FIG. 1 illustrates a typical SCS system implanted in a patient. As can be seen, the system comprises a pulse generator such as an SCS neurostimulator 20, a lead extension 22 having a proximal end coupled to neurostimulator 20 as will be more fully described below, and a lead 24 having proximal end coupled to the distal end of extension 22 and having a distal end coupled to one or more electrodes 26. Neurostimulator 20 is typically placed in the abdomen of a patient 28, and lead 24 is placed somewhere along spinal cord 30. As stated previously, neurostimulator 20 may have one or two leads each having four to eight electrodes. Such a system may also include a physician programmer and a patient programmer (not shown). Neurostimulator 20 may be considered to be an implantable pulse generator of the type available from Medtronic, Inc. and capable of generating multiple pulses occurring either simultaneously or one pulse shifting in time with respect to the other, and having independently varying amplitudes and pulse widths. Neurostimulator 20 contains a power source and the electronics for sending precise, electrical pulses to the spinal cord to provide the desired treatment therapy. While neurostimulator 20 typically provides electrical stimulation by way of pulses, other forms of stimulation may be used as continuous electrical stimulation.

Lead 24 is a small medical wire having special insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). Lead 24 may contain a paddle at its distant end for housing electrodes 26; e.g. a Medtronic paddle having model number 3587A. Alternatively, electrodes 26 may comprise one or more ring contacts at the distal end of lead 24 as will be more fully described below.

While lead 24 is shown as being implanted in position to stimulate a specific site, in spinal cord 30, it could also be positioned along the peripheral nerve or adjacent neural tissue ganglia or may be positioned to stimulate muscle tissue. Furthermore, electrodes 26 may be epidural, intrathecal or placed into spinal cord 30 itself. Effective spinal cord stimulation may be achieved by any of these lead placements. While the lead connector at proximal end of lead 24 may be coupled directly to neurostimulator 20, the lead connector is typically coupled to lead extension 22 as is shown in FIG. 1. An example of a lead extension is Model 7495 available from Medtronic, Inc.

A physician's programmer (not shown) utilizes telemetry to communicate with the implanted neurostimulator 20 to enable the physician to program and manage a patient's therapy and troubleshoot the system. A typical physician's programmer is available from Medtronic, Inc. and bears Model No. 7432. Similarly, a patient's programmer (also not shown) also uses telemetry to communicate with neurostimulator 20 so as to enable the patient to manage some aspects of their own therapy as defined by the physician. An example of a patient programmer is Model 7434® 3 EZ Patient Programmer available from Medtronic, Inc.

Implantation of a neurostimulator typically begins with the implantation of at least one stimulation lead usually while the patient is under a local anesthetic. While there are many spinal cord lead designs utilized with a number of different implantation techniques, the largest distinction between leads revolves around how they are implanted. For example, surgical leads have been shown to be highly effective, but require a laminectomy for implantation. Percutaneous leads can be introduced through a needle, a much easier procedure. To simplify the following explanation, discussion will focus on percutaneous lead designs, although it will be understood by those skilled in the art that the inventive aspects are equally applicable to surgical leads. After the lead is implanted and positioned, the lead's distal end is typically anchored to minimize movement of the lead after implantation. The lead's proximal end is typically configured to connect to a lead extension 22. The proximal end of the lead extension is then connected to the neurostimulator 20.

Figure 2:
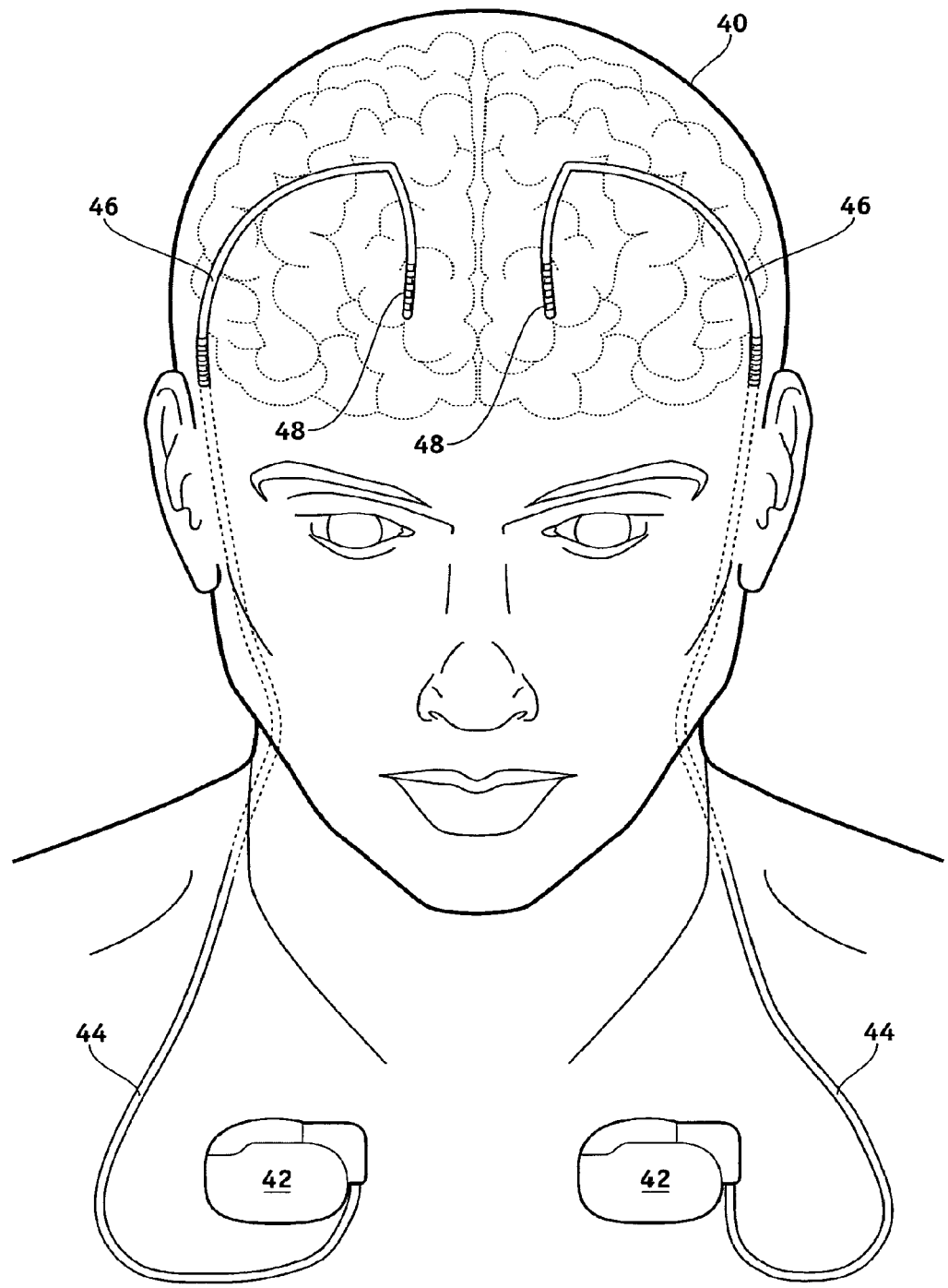
FIG. 2 illustrates a typical deep brain stimulation system implanted in a patient.

FIG. 2 illustrates a DBS system implanted in a patient 40 and comprises substantially the same components as does an SCS; that is, at least one neurostimulator, at least one extension, and at least one stimulation lead containing one or more electrodes. As can be seen, each neurostimulator 42 is implanted in the pectoral region of the patient. Extensions 44 are deployed up through the patient's neck, and leads 46 are implanted in the patient's brain is as shown at 48. As can be seen, each of the leads 46 is connected to its respective extension 44 just above the ear on both sides of patient 40.

Figure 5:
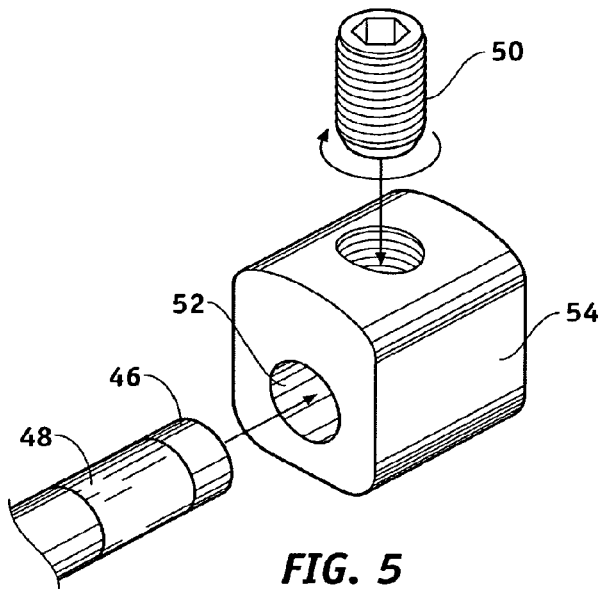
FIG. 5 is an isometric view of an example of a connector screw block suitable for connecting the lead of FIG. 3 to the extension shown in FIG. 4.
Figure 3:
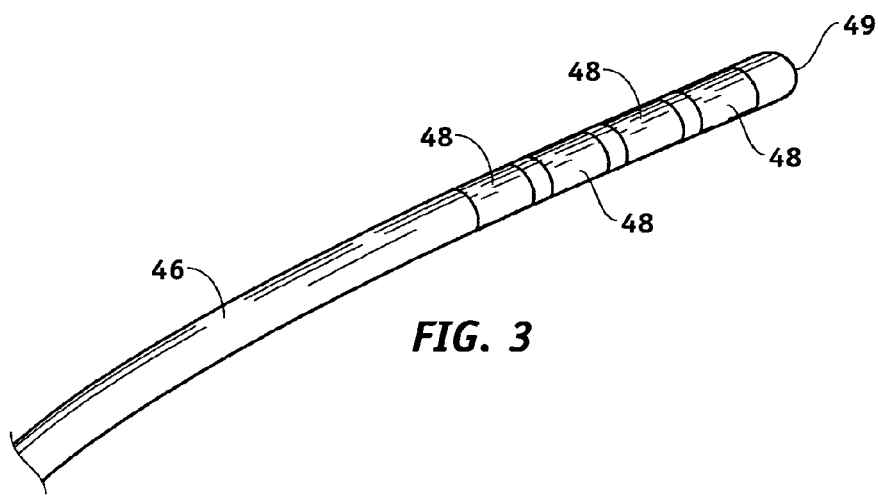
FIG. 3 is an isometric view of the distal end of the lead shown in FIG. 2.
Figure 4:
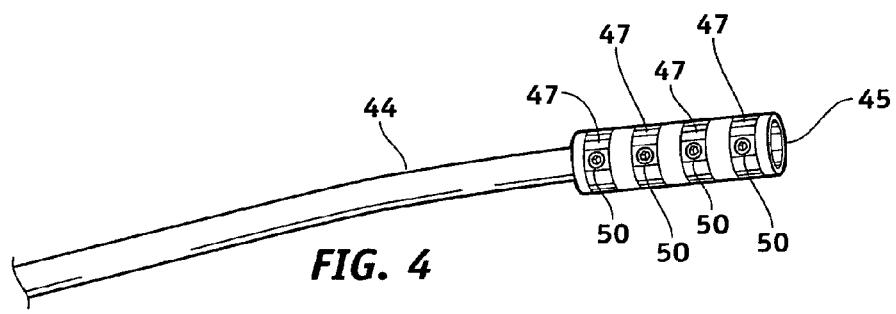
FIG. 4 is an isometric view of the distal end of the extension shown in FIG. 2.

FIG. 3 is an isometric view of the distal end of lead 46. In this case, four ring electrodes 48 are positioned on the distal end of lead 46 and coupled to internal conductors of filers (not shown) contained within lead 46. Again, while four ring electrodes are shown in FIG. 3, it is to be understood that the number of electrodes can vary to suit a particular application. FIG. 4 is an isometric view of the distal end of extension 44, which includes a connector portion 45 having four internal contacts 47. The proximal end of the DBS lead is shown in FIG. 3, plugs into the distal connector 45 of extension 44, and is held in place by means of, for example, a plurality (e.g. 4) of set screws 50. For example, referring to FIG. 5, lead 46 terminates in a series of proximal electrical ring contacts 48 (only one of which is shown in FIG. 5). Lead 46 may be inserted through an axially aligned series of openings 52 (again only one shown) in screw block 54. With a lead 46 so inserted, a series of set screws (only one shown) are screwed into block 54 to drive contacts 48 against blocks 54 and secure and electrically couple the lead 46. It should be appreciated, however, that other suitable methods for securing lead 46 to extension 44 may be employed. The proximal portion of extension 44 is secured to neurostimulator 42 as is shown in FIGS. 1 and 2.

FIG. 6 is a top view of lead 46 shown in FIG. 2. FIGS. 7 and 8 are cross-sectional views taken along lines 7-7 and 8-8, respectively, in FIG. 6. Distal end 60 of lead 46 includes at least one electrode 62 (four are shown). As stated previously, up to eight electrodes may be utilized. Each of electrodes 62 is preferably constructed as is shown in FIG. 8. That is, electrode 62 may comprise a conductive ring 71 on the outer surface of the elongate tubing making up distal shaft 60. Each electrode 62 is electrically coupled to a longitudinal wire 66 (shown in FIGS. 7 and 8) each of which extends to a contact 64 at the proximal end of lead 46. Longitudinal wires 66 may be of a variety of configurations; e.g. discreet wires, printed circuit conductors, etc. From the arrangement shown in FIG. 6, it should be clear that four conductors or filers run through the body of lead 46 to electrically connect the proximal electrodes 64 to the distal electrodes 62. As will be further discussed below, the longitudinal conductors 66 may be spirally configured along the axis of lead 46 until they reach the connector contacts.

The shaft of lead 46 preferably has a lumen 68 extending therethrough for receiving a stylet that adds a measure of rigidity during installation of the lead. The shaft preferably comprises a comparatively stiffer inner tubing member 70 (e.g. a polyamine, polyamide, high density polyethylene, polypropylene, polycarbonate or the like). Polyamide polymers are preferred. The shaft preferably includes a comparatively softer outer tubing member 72; e.g. silicon or other suitable elastomeric polymer. Conductive rings 71 are preferably of a biocompatible metal such as one selected from the noble group of metals, preferably palladium, platinum or gold and their alloys.

FIG. 9 illustrates an alternative lead 74 wherein distal end 76 is broader (e.g. paddle-shaped) to support a plurality of distal electrodes 78. A lead of this type is shown in FIG. 1. As was the case with the lead shown in FIGS. 6,7, and 8, distal electrodes 78 are coupled to contacts 64 each respectively by means of an internal conductor or filer. A more detailed description of the leads shown in FIGS. 6 and 9 may be found in U.S. Pat. No. 6,529,774 issued Mar. 4, 2003 and entitled "Extradural Leads, Neurostimulator Assemblies, and Processes of Using Them for Somatosensory and Brain Stimulation".

Figure 11:
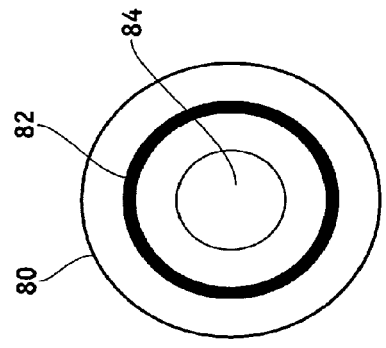
FIGS. 10 and 11 are longitudinal and radial cross-sectional views of a helically wound lead of the type shown in FIG. 6.
Figure 10:
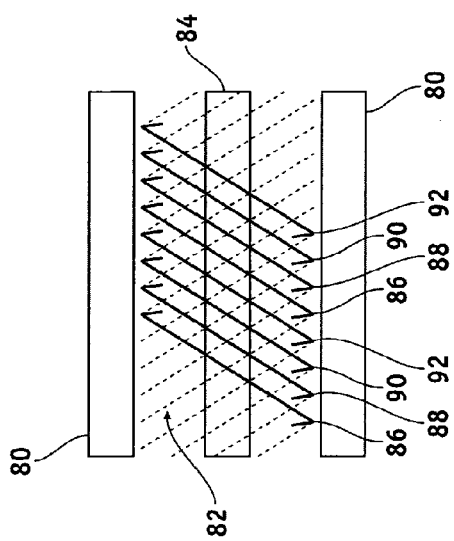

Leads of the type described above may be of the wound helix filer type or of the cabled filer type. FIGS. 10 and 11 are longitudinal and radial cross-sectional views, respectively, of a helically wound lead of the type shown in FIG. 6. The lead comprises an outer lead body 80; a plurality of helically wound, co-radial lead filers 82; and a stylet lumen 84. As stated previously, a stylet is a stiff, formable insert placed in the lead during implant so as to enable the physician to steer the lead to an appropriate location. FIG. 10 illustrates four separate, co-radially wound filers 86, 88, 90, and 92 which are electrically insulated from each other and electrically couple a single electrode 62 (FIG. 6) to a single contact 64 (FIG. 6).

Figure 13:
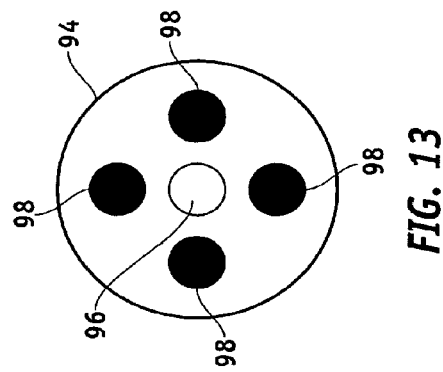
FIGS. 12 and 13 are longitudinal and radial cross-sectional views, respectively, of a cabled lead.
Figure 12:
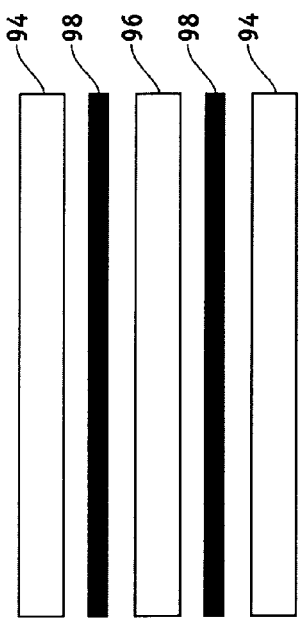

As can be seen, lead filers 82 have a specific pitch and form a helix of a specific diameter. The helix diameter and pitch are relevant in determining the inductance of the lead. These filers themselves also have a specific diameter and are made of a specific material. The filer diameter, material, pitch and helix diameter are relevant in determining the impedance of the lead. In the case of a helically wound lead, the inductance contributes to a frequency dependent impedance. FIGS. 12 and 13 are longitudinal and radially cross-sectional views, respectively, of a cabled lead. The lead comprises outer lead body 94, stylet lumen 96, and a plurality (e.g. four to eight) of straight lead filers 98.

Figure 14:
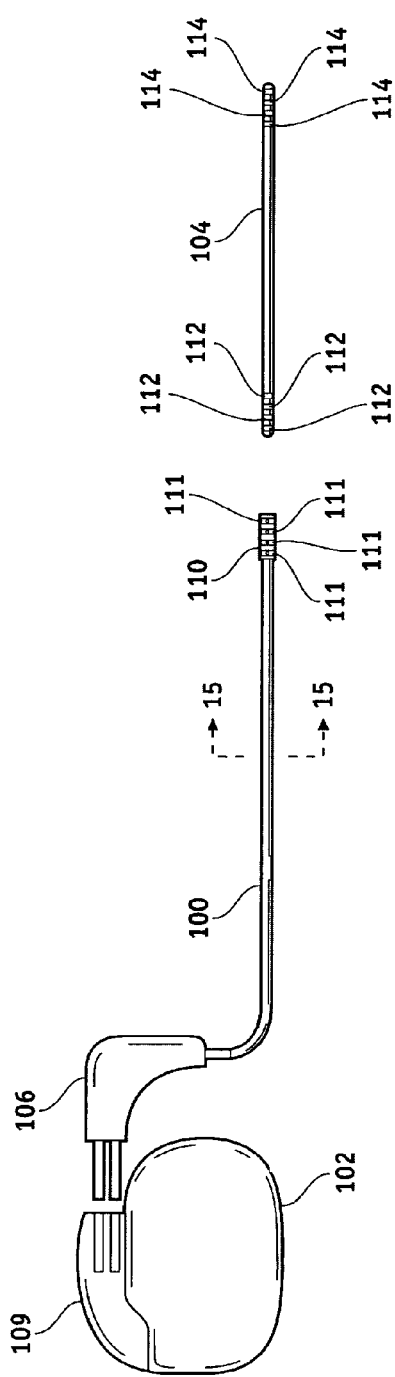
FIG. 14 is an exploded view of a neurostimulation system.

FIG. 14 is an exploded view of a neurostimulation system that includes an extension 100 configured to be coupled between a neurostimulator 102 and lead 104. The proximal portion of extension 100 comprises a connector 106 configured to be received or plugged into connector block 109 of neurostimulator 102. The distal end of extension 100 likewise comprises a connector 110 including internal contacts 111 and is configured to receive the proximal end of lead 104 having contacts 112 thereon. The distal end of lead 104 includes distal electrodes 114.

Figure 15:
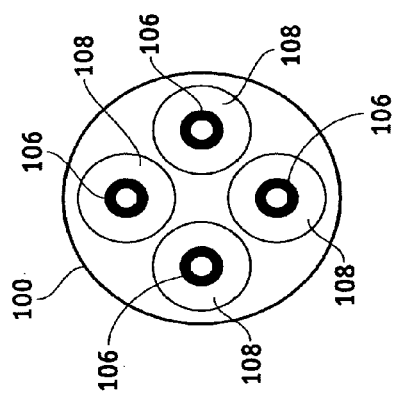
FIG. 15 is a cross-sectional view of the extension shown in FIG. 14 taken along line 15-15.

FIG. 15 is a cross-sectional view of extension 100. Lead extension 100 has a typical diameter of 0.1 inch, which is significantly larger than that of lead 104 so as to make extension 100 more durable than lead 104. Extension 100 differs from lead 104 also in that each filer 106 in lead body is helically wound or coiled in its own lumen 108 and not co-radially wound with the rest of the filers as was the case in lead 104.

The diameter of typical percutaneous leads is approximately 0.05 inch. This diameter is based upon the diameter of the needle utilized in the surgical procedure to deploy the lead and upon other clinical anatomical requirements. The length of such percutaneous SCS leads is based upon other clinical anatomical requirements. The length of such percutaneous SCS leads is typically 28 centimeters; however, other lengths are utilized to meet particular needs of specific patients and to accommodate special implant locations.

Lead length is an important factor in determining the suitability of using the lead in an MRI environment. For example, the greater length of the lead, the larger the effective loop area that is impacted by the electromagnetic field (e.g. the longer the lead, the larger the antenna). Furthermore, depending on the lead length, there can be standing wave effects that create areas of high current along the lead body. This can be problematic if the areas of high current are near the distal electrodes.

Compared to the helically wound lead, the cable lead has smaller DC resistance because the length of the straight filer is less than that of a coiled filer and the impedance at frequency is reduced because the inductance has been significantly reduced. It has been determined that the newer cabled filer designs tend to be more problematic in an MRI environment than do the wound helix filer designs. It should be noted that straight filers for cable leads sometimes comprise braided stranded wire that includes a number of smaller strands woven to make up each filer. This being the case, the number of strands could be varied to alter the impedance.

As stated previously, the electromagnetic fields within an MRI or diathermy environment produce RF currents in the leads that can result in the production of heat and accompanying undesirable temperature increases at the lead electrodes. This problem may be mitigated by shielding the lead filers from the electromagnetic field, thus reducing the amount of energy reaching lead filers, and therefore decreasing the extent to which the electrodes are heated. This shielding of the filers from the electromagnetic field may be accomplished through the use of a number of methods and conductive materials. Since the problem which is to be solved relates to an implanted lead, any shielding material should preferably be bio-compatible and corrosion-resistant. Examples of such materials are titanium, stainless steel and platinum. These metals may be used to form sheets, braids, wires, coils (of a constant or variable pitch), foils or powders. Additional suitable materials include gold-plated microspheres, solid particles of conductive polymers, carbon powder, carbon fibers, and intrinsically conductive polymers.

These shielding materials and formats may be incorporated into the implantable lead in a number of ways that permit contact between the shield and the patient's body. For example, a shield could be co-extruded with the lead jacket tubing. Co-extrusion is a well-known process and could be employed using the shielding materials listed above. Since co-extrusion would most likely result in the suspension of the shield inside the jacket, openings or holes may be formed in the jacket as, for example, by drilling in order to provide the desired contact with the patient's body. Alternatively, the shield could be placed in contact with the housing of the implanted medical device which is, in turn, in contact with the patient's body. If desired, the shield could be mechanically coupled or attached to the exterior surface of the lead. This may be accomplished utilizing a metal braid tube or metal sheet, wire, or foil. The tube, sheet, wire, or foil could be simply adhered to the exterior jacket of the lead by, for example, polyurethane, silicone, and epoxy type adhesives. Alternatively, the shield may be comprised of a separate element which covers the lead. For example, the shield could be configured to reside around the lead without being attached or adhered to the lead surface.

Other possible methodologies include shielding the lead by imbedding, depositing, implanting, bombarding, coextruding, or ionic plasma deposition. Shielding material may be deposited along with vapor deposited material such as paralene using a vapor deposition process. A shielding material may be electrochemically deposited onto the jacket to shield the lead, or a bio-compatible organic coating may be bound to the surface of the jacket which is infused with shielding material or to which shielding material may be bound. Other known techniques may also be employed.

FIG. 16 is a cross-sectional view of a multi-layer composite jacket comprised of alternating layers of conductive material 120 and 122 and non-conductive material 124. These layers together form an electromagnetic shield. While FIG. 16 illustrates two conductive layers and an intermediate non-conductive layer, it should be clear that the number of alternating layers may be increased to suit a particular purpose. Preferably, conductive layer 120 is configured so as to reside in direct contact with a patient's body tissue; however, irrespective of whether the outer layer is conductive or not conductive, a level of shielding of the lead filers is achieved. Inner conductive layer 122 may be configured to contact the patient's body tissue through the encasement of the implanted medical device or through pores in the outer layers of the jacket. For example, FIG. 17 is a cross-sectional view illustrating a composite shield 126 of the type shown in FIG. 16 surrounded by a jacket 128 having a plurality of pores 130 therethrough so as to enable contact between the patient's body tissue or fluids and shield composite 126.

As already stated to, it would be desirable that the lead shield be configured to have good RF electromagnetic contact with the surrounding body tissue. In this manner, energy created in the shield during an MRI scan can be safely dissipated in the surrounding tissue. Additionally, if the shield is in direct contact with the patient's body, the shield does not retransmit energy to the lead filers. It has already been shown in connection with FIG. 17 that pores in jacket 128 may be utilized to provide contact between the patient's body tissue and shield 126. Such contact may be accomplished in a number of other ways, examples of which are described in the following paragraphs.

In order to assure that energy created in the shield is safely dissipated, the shield may be configured to be in direct contact with body tissue. This may be accomplished by adhering the shield to the exterior surface of the jacket. The shield may be electrochemically deposited onto the jacket, or it may be configured as a coating on the exterior surface of the jacket. If desired, the shield can be configured so that it merely resides near the exterior surface of the lead so as to easily transmit absorbed RF energy to body tissue. For example, if the outer layer of the multi-layer composite jacket were extremely thin, the energy created in the shield could be easily transmitted to the surrounding tissue.

Figure 19:
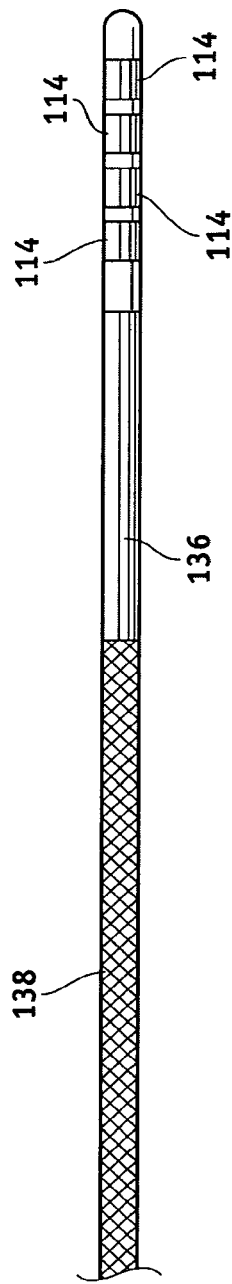
FIG. 19 is a side view of a still further embodiment of the present invention utilizing a grounding electrode.
Figure 20:
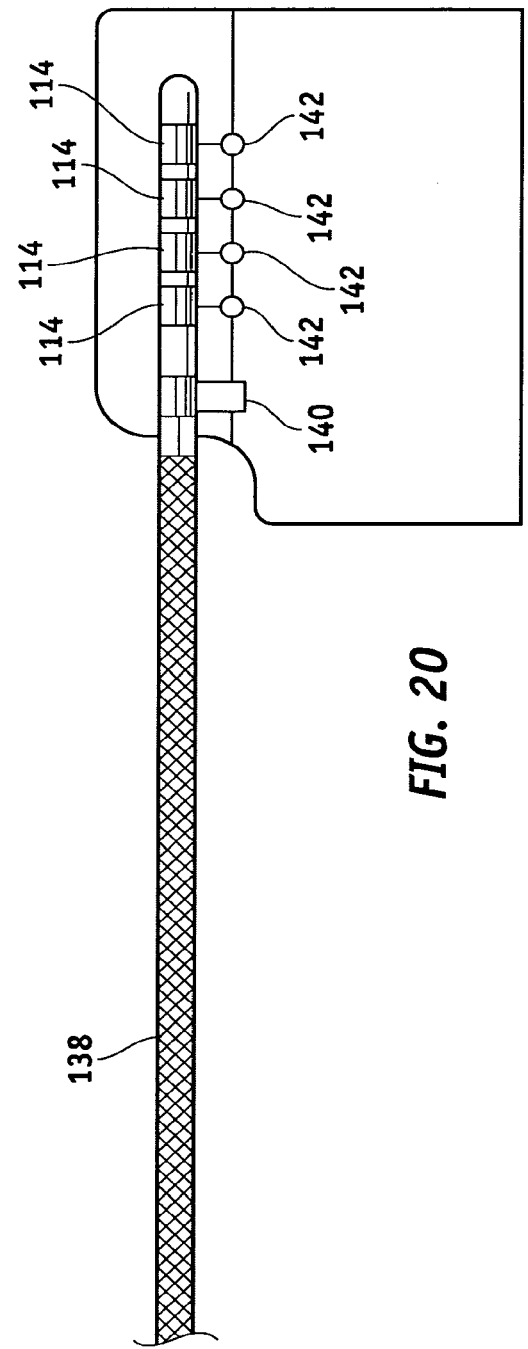
FIG. 20 is a side view of yet another embodiment of the present invention wherein the shield is coupled to a conductive encasement of an implantable pulse generator.

FIG. 18 illustrates a lead configuration wherein floating electrodes 132 are placed at desired locations along the length of the lead separated by shield segments 134 to assure that the shield is in contact with the patient's body tissue. If desired, the shield may be electrically coupled to a grounding electrode somewhere along the length of the lead. This grounding electrode may be a separate electrode somewhere on the lead or it could be the conductive encasement of the implantable pulse generator itself. FIG. 19 illustrates such a grounding electrode 136 coupled to shield 138. In FIG. 20, shield 138 is coupled to the IPG encasement 140 by means of a shield-to-case connector 140 and a plurality of feedthrough connections 142 which couple encasement 140 to electrodes 114.

While the shield may extend substantially the entire length of the lead, the shield could be segmented to prevent absorbed RF energy from developing a standing wave along the length of the lead or extension if desired. This segmentation may be accomplished by physically severing the shield at various locations along the length of the lead or by grounding the shield to the surrounding tissue along the lead. The length of each segment should not be substantially greater than one-quarter wavelength. This configuration is shown in FIG. 21 wherein a plurality of grounding sections 144 divide the shield into shielding segments 146.

Alternatively, to prevent the formation of standing waves, the shield could be constructed such that no continuous conductive paths exist along the length of the lead. This may be accomplished by doping the lead jacket with conductive particles such that they do not form a good conductive path along the length of the lead.

It may be desirable to form the shielding so as to increase the current conduction paths of absorbed RF energy to help dissipate the RF energy as heat along the length of the lead. This may be accomplished, for example, by doping the lead jacket with solid particles of conductive materials (e.g. metals, polymers, etc.), embedding a braided metal wire in the lead jacket with an opening size that is much greater than (e.g. ten times greater) than the diameter of the wire, and/or utilizing one or more layers of metal foil embedded in the jacket.

Figure 22:
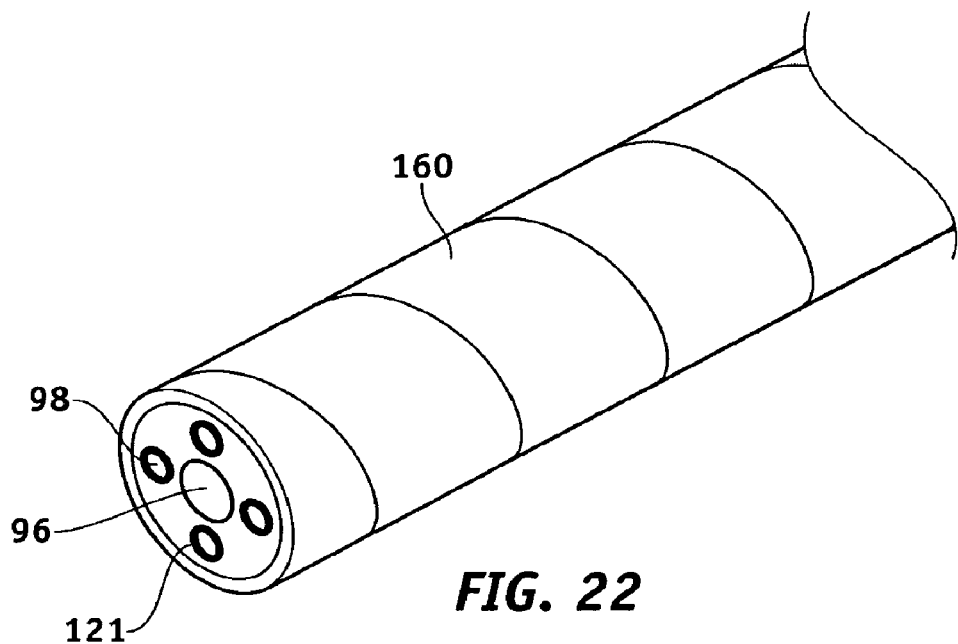
FIGS. 22 and 23 illustrate yet another embodiment of the present invention.
Figure 23:
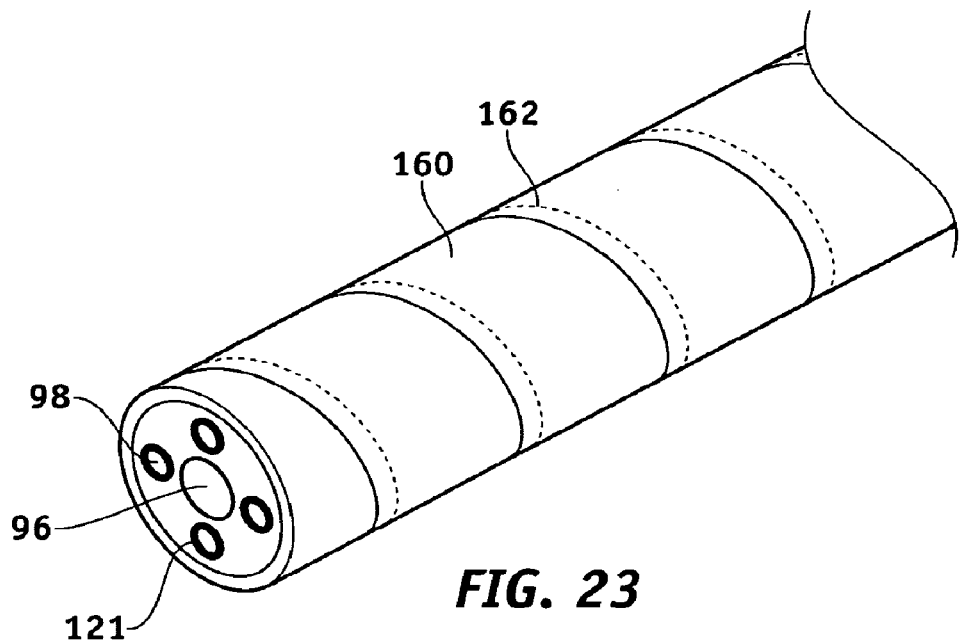

As stated previously, FIG. 16 is a cross-sectional view of a multi-layer composite jacket comprised of alternating layers of conductive and non-conductive material 120 and 122 respectively; e.g. alternating layers of Teflon™ impregnated to be conductive or non-conductive. The alternating layers may be produced by, for example, co-extrusion, dispersion coating, vapor deposition or atomized coating in accordance with know techniques; or alternatively, the lead jacket could be wrapped with alternating conductive and non-conductive layers. This could be done using two conductive layers (e.g. doped Teflon™ or PTFE) and one dielectric layer (e.g. PTFE doped with a dielectric material). FIGS. 22 and 23 show a lead including four filers 98 each provided with insulation 121 and a stylet 96. Layers could be, for example, extruded or wrapped. Preferably, the two conductive layers are wrapped and the intermediate non-conductive layer is extruded. In FIG. 22, the layers 160 are wrapped in an edge-abutting manner, whereas in FIG. 23, the layers are wrapped in an overlapping manner as indicated by dotted line 162.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A neurostimulation system configured to be implanted into a patient's body comprising: a neurostimulator and a lead, the lead having at least one distal electrode, the lead comprising:
   at least one conductive filer electrically coupled to the distal electrode;
   a non-conductive jacket for housing said conductive filer and having at least one layer comprising a non-conductive material that provides an outer surface configured to contact the patient's body; and
   a shield comprising a continuous portion that has a first physically severed end and a second physically severed end and that comprises metal wire surrounding at least a portion of said filer for reducing electromagnetic coupling to said filer, wherein the shield resides within the jacket beneath the at least one layer of the jacket so that the continuous portion of the shield is completely surrounded by the non-conductive jacket from the first physically severed end to the second physically severed end so that a pathway for electromagnetic energy from the shield to the outer surface of the jacket is provided through the non-conductive material of the at least one layer of the jacket, and wherein the embedded shield allows radio frequency energy absorbed by the shield to be transmitted out of the outer surface of the jacket.

2. A neurostimulation system according to claim 1 wherein said shield comprises a plurality of separate shield segments.

3. A neurostimulation system according to claim 2 wherein said segments are substantially one-quarter wavelength of RF energy being applied to the shield in length.

4. A neurostimulation system according to claim 1 wherein said shield comprises tantalum.

5. A neurostimulation system according to claim 1 wherein said shield comprises metal along substantially its entire length.

6. A neurostimulation system according to claim 1 wherein said shield comprises a braid.

7. The neurostimulation system according to claim 1 wherein the shield comprises platinum.

8. The neurostimulation system according to claim 1 wherein the shield comprises titanium.

9. The neurostimulation system according to claim 1 wherein the shield comprises stainless steel.

10. The neurostimulation system according to claim 1 wherein the shield comprises chromium cobalt.

11. The neurostimulation system according to claim 1 wherein the shield comprises nitinol.

12. The neurostimulation system according to claim 1 wherein the shield comprises iridium.

13. The neurostimulation system according to claim 1 wherein the non-conductive material comprises a polymer.

14. A neurostimulation system configured to be implanted into a patient's body comprising: a neurostimulator and a lead, the lead having at least one distal electrode, the lead comprising:

at least one conductive filer electrically coupled to the distal electrode;

a polymer jacket for housing said conductive filer and having at least one layer comprising a polymer that provides an outer surface configured to contact the patient's body; and a shield comprising a continuous portion that has a first physically severed end and a second physically severed end and that comprises metal wire surrounding at least a portion of said filer for reducing electromagnetic coupling to said filer, wherein the shield resides within the jacket beneath the at least one layer of the jacket so that the continuous portion of the shield is completely surrounded by the polymer jacket from the first physically severed end to the second physically severed end so that a pathway for electromagnetic energy from the shield to the outer surface of the jacket is provided through the polymer of the at least one layer of the jacket, and wherein the embedded shield allows radio frequency energy absorbed by the shield to be transmitted out of the outer surface of the jacket.

\* \* \* \* \*